(12) United States Patent
Urata et al.

(10) Patent No.: US 7,276,536 B2
(45) Date of Patent: Oct. 2, 2007

(54) METHOD FOR INCREASING THE BIOAVAILABILITY OF THE ACTIVE FORM OF S-[2-([[1-(2-ETHYLBUTYL)CYCLO-HEXYL]CARBONYL]AMINO) PHENYL] 2-METHYLPROPANETHIOATE

(75) Inventors: Yasuo Urata, Tokyo (JP); Tomohiro Ishikawa, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 318 days.

(21) Appl. No.: 10/802,280

(22) Filed: Mar. 17, 2004

(65) Prior Publication Data

US 2004/0242683 A1 Dec. 2, 2004

Related U.S. Application Data

(60) Provisional application No. 60/477,202, filed on Jun. 10, 2003, provisional application No. 60/460,521, filed on Apr. 4, 2003, provisional application No. 60/455,293, filed on Mar. 17, 2003.

(51) Int. Cl.
*A61K 31/21* (2006.01)
(52) U.S. Cl. ..................................... 514/513
(58) Field of Classification Search ............... None
See application file for complete search history.

(56) References Cited

U.S. PATENT DOCUMENTS

| | | | |
|---|---|---|---|
| 3,576,830 A | 4/1971 | Fukumaru et al. |
| 4,346,277 A | 8/1982 | Wojtecki et al. |
| 4,444,784 A | 4/1984 | Hoffman et al. |
| 4,681,893 A | 7/1987 | Roth |
| 4,740,438 A | 4/1988 | Krishnamurthy |
| 4,853,319 A | 8/1989 | Krishnamurthy et al. |
| 5,011,930 A | 4/1991 | Fujikawa et al. |
| 5,030,447 A | 7/1991 | Joshi et al. |
| 5,118,583 A | 6/1992 | Kondo et al. |
| 5,180,589 A | 1/1993 | Joshi et al. |
| 5,194,539 A | 3/1993 | Charmot et al. |
| 5,217,859 A | 6/1993 | Boettcher et al. |
| 5,219,721 A | 6/1993 | Klaus et al. |
| 5,260,440 A | 11/1993 | Hirai et al. |
| 5,273,995 A | 12/1993 | Roth |
| 5,350,667 A | 9/1994 | Singer et al. |
| 5,354,772 A | 10/1994 | Kathawala |
| 5,356,896 A | 10/1994 | Kabadi et al. |
| 5,405,969 A | 4/1995 | Wright et al. |
| 5,446,207 A | 8/1995 | Pomponi et al. |
| 5,504,097 A | 4/1996 | Malamas et al. |
| 5,512,548 A | 4/1996 | Kushwaha et al. |
| 5,519,001 A | 5/1996 | Kushwaha et al. |
| 5,534,529 A | 7/1996 | Yoshida et al. |
| 5,542,974 A | 8/1996 | Buding |
| 5,556,888 A | 9/1996 | Koda et al. |
| 5,614,550 A | 3/1997 | Yoshida et al. |
| 5,622,985 A | 4/1997 | Olukotun et al. |
| 5,654,134 A | 8/1997 | Morimura et al. |
| 5,686,104 A | 11/1997 | Mills et al. |
| 5,698,564 A | 12/1997 | Katsuyama et al. |
| 5,776,951 A | 7/1998 | Arrowsmith et al. |
| 5,880,095 A | 3/1999 | Park et al. |
| 5,916,595 A | 6/1999 | Chen et al. |
| 5,925,645 A | 7/1999 | Schmidt et al. |
| 5,932,587 A | 8/1999 | Schmeck et al. |
| 5,969,156 A | 10/1999 | Briggs et al. |
| RE36,481 E | 1/2000 | Inamine et al. |
| RE36,520 E | 1/2000 | Smith et al. |
| 6,069,148 A | 5/2000 | Schmidt et al. |
| 6,080,778 A | 6/2000 | Yankner et al. |
| 6,093,573 A | 7/2000 | Beamer et al. |
| 6,126,971 A | 10/2000 | Mills et al. |
| 6,127,383 A | 10/2000 | Schmidt et al. |
| 6,140,342 A | 10/2000 | Goldstein et al. |
| 6,140,343 A | 10/2000 | DeNinno et al. |
| 6,147,089 A | 11/2000 | DeNinno et al. |
| 6,147,090 A | 11/2000 | DeNinno et al. |
| 6,197,786 B1 | 3/2001 | DeNinno et al. |
| 6,207,671 B1 | 3/2001 | Schmidt et al. |
| 6,242,003 B1 | 6/2001 | Kalb et al. |
| 6,313,142 B1 | 11/2001 | Damon et al. |

(Continued)

FOREIGN PATENT DOCUMENTS

| | | |
|---|---|---|
| CA | 2000631 A | 4/1990 |
| EP | 0 533 281 A1 | 3/1993 |
| EP | 0 796 846 A1 | 9/1997 |
| EP | 0 818 197 A1 | 1/1998 |
| EP | 0 818 448 A1 | 1/1998 |
| EP | 0 992 496 A1 | 4/2000 |
| EP | 1 269 994 A2 | 1/2003 |
| ES | 2127690 B1 | 4/1999 |
| JP | 45-11132 | 4/1970 |

(Continued)

OTHER PUBLICATIONS

Okamotot et al., Nature, vol. 406, Jul. 13, 2000, pp. 203-207.*
Harrison's Principle of Internal Medicine, 13th Ed., vol. 1, published in 1994 by McGraw-Hill, Inc., pp. 1108-1116.*
Jones et al., "The Curves Study", The American Journal of Cardiology, vol. 81, Mar. 1, 1998, pp. 582-587.*
The Merck Manual of Diagnosis of Therapy, 14th Ed., published 1982 by Merck, Sharp & Dohme Research Laboratories, pp. 386-389 and 550-555.*

(Continued)

*Primary Examiner*—Raymond J. Henley, III
(74) *Attorney, Agent, or Firm*—Leydig, Voit & Mayer, Ltd.

(57) ABSTRACT

The invention is directed to a method of increasing the bioavailability of the active form of S-[2-([[1-(2-ethylbutyl)cyclohexyl]carbonyl]amino)phenyl]2-methylpropanethioate by administration of a therapeutically effective amount of the drug with food. The invention also provides a kit comprising a pharmaceutical composition comprising a therapeutically effective amount of S-[2-([[1-(2-ethylbutyl)cyclohexyl]carbonyl]amino)phenyl]2-methylpropanethioate and a pharmaceutically acceptable carrier, prescribing information, and a container, wherein the prescribing information includes advice to a patient regarding administration of the drug with food to improve bioavailability.

70 Claims, 5 Drawing Sheets

U.S. PATENT DOCUMENTS

| | | |
|---|---|---|
| 6,362,198 B1 | 3/2002 | Goldstein et al. |
| 6,395,751 B1 | 5/2002 | DeNinno et al. |
| 6,426,365 B1 | 7/2002 | Shinkai et al. |
| 6,448,295 B1 | 9/2002 | Sikorski et al. |
| 6,462,091 B1 | 10/2002 | Keller et al. |
| 6,753,346 B2 | 6/2004 | Shinkai et al. |
| 2001/0018446 A1 | 8/2001 | Sikorski et al. |
| 2002/0103225 A1 | 8/2002 | Curatolo et al. |
| 2004/0039018 A1 | 2/2004 | Ruggeri |
| 2004/0053842 A1 | 3/2004 | Nguyen et al. |
| 2006/0014788 A1* | 1/2006 | Gumkowski et al. ........ 514/313 |

FOREIGN PATENT DOCUMENTS

| | | |
|---|---|---|
| JP | 47-35786 | 9/1972 |
| JP | 1-278543 | 11/1989 |
| JP | 1-321432 | 12/1989 |
| JP | 2-23338 | 1/1990 |
| JP | 3-226750 | 10/1991 |
| JP | 9-59155 A | 3/1997 |
| JP | 10-287662 A | 10/1998 |
| WO | WO 92/03408 A1 | 3/1992 |
| WO | WO 92/03412 A2 | 3/1992 |
| WO | WO 96/09406 A1 | 3/1996 |
| WO | WO 96/30761 A1 | 10/1996 |
| WO | WO 98/04528 A2 | 2/1998 |
| WO | WO 98/23593 A1 | 6/1998 |
| WO | WO 98/34920 A1 | 8/1998 |
| WO | WO 98/35937 A1 | 8/1998 |
| WO | WO 98/39299 A1 | 9/1998 |
| WO | WO 99/14204 A1 | 3/1999 |
| WO | WO 99/41237 A1 | 8/1999 |
| WO | WO 99/50454 A2 | 10/1999 |
| WO | WO 98/04528 A3 | 11/1999 |
| WO | WO 00/17164 A1 | 3/2000 |
| WO | WO 00/18721 A1 | 4/2000 |
| WO | WO 00/18723 A1 | 4/2000 |
| WO | WO 00/18724 A1 | 4/2000 |
| WO | WO 00/38721 A1 | 7/2000 |
| WO | WO 00/38722 A1 | 7/2000 |
| WO | WO 00/38723 A1 | 7/2000 |
| WO | WO 00/38724 A1 | 7/2000 |
| WO | WO 00/38725 A1 | 7/2000 |
| WO | WO 00/38726 A1 | 7/2000 |
| WO | WO 00/53792 A1 | 9/2000 |
| WO | WO 01/18250 A2 | 3/2001 |
| WO | WO 01/40190 A1 | 6/2001 |
| WO | WO 01/56579 A1 | 8/2001 |
| WO | WO 02/11710 A2 | 2/2002 |
| WO | WO 02/11710 A3 | 5/2002 |
| WO | WO 01/18250 A3 | 7/2002 |
| WO | WO 02/059077 A1 | 8/2002 |
| WO | WO 03/000235 A1 | 1/2003 |
| WO | WO 03/000295 A2 | 1/2003 |
| WO | WO 03/063832 A1 | 8/2003 |
| WO | WO 03/000295 A3 | 5/2004 |
| WO | WO 2004/082593 A2 | 9/2004 |
| WO | WO 2004/082675 A1 | 9/2004 |
| WO | WO 2004/098583 A1 | 11/2004 |

OTHER PUBLICATIONS

Webster's II, New Riverside University Dictionary, published in 1984 by Houghton Mifflin Co., "food" entry, p. 494.*

Handbook of Pharmaceutical Excipients, published 1986 by the American Pharmaceutical Association (DC), pp. 153-162 and 289-293.*

Remington's Pharmaceutical Sciences, 16th Edition, published 1980 by Mack Publishing, Inc., pp. 1715-1728 and 1855-1857.*

Remington's Pharmaceutical Sciences, Osol et al., (Eds.), 16th edition, published 1980, p. 1855.*

Antonova et al., *Comptes rendus de I'Academie bulgare des Sciences*, 46(1), 71-74 (1993).

Connolly et al., *Biochemical and Biophysical Research Communications*, 223(1), 42-47 (1996).

De Grooth et al., *XIV International Symposium on Drugs Affecting Lipid Metabolism*, 47 (2001).

De Grooth et al., *Circulation, Supplement II*, 104(17), 848 (2001).

Drozd, *Zhurnal Organicheskoi Khimii*, 23(2), 355-365 (1987).

Egan et al., *Advances in Prostaglandin, Thromboxane, and Leukotriene Research*, 11, 151-157 (1983).

Hori et al., *Heterocycles* 9(10), 1413-1418 (1978).

Huang et al., *Clinical Science*, 103(6), 587-594 (2002).

Maeda et al., *Bioorganic & Medicinal Chemistry Letters*, 14, 2589-2591 (2004).

Nagarajan et al., *Indian Journal of Chemistry*, 12(3), 227-235 (1974).

Okamoto, *Lipid*, 13(1), 76-81 (2002).

Okamoto, *BIO Clinica*, 18(5), 429-432 (2003).

Okamoto et al., *European Journal of Pharmacology*, 466(1-2), 147-154 (2003).

Shimoji et al., *Atherosclerosis*, 172(2), 247-257 (2004).

Shinkai, *Naibunpi, Tonyobyoka*, 12(4), 364-369 (2001).

Simov et al., *Khimya Geterotsiklicheskikh Soedinenii*, 9, 1192-1195 (1976).

Wakitani et al., *The Knowledge Foundation's 2nd International Conference on HDL Cholesterol Metabolic Pathways and Drug Development*, 1 (2001).

Watts, *Clinical Science*, 103(6), 595-597 (2002).

WCN Working Group on Cardiovascular Research, *Slide Presented at the 15th Annual Scientific WCN Meeting*, Amsterdam, The Netherlands (Dec. 2002).

Inazu et al., *Current Opinion in Investigational Drugs*, 4(3): 291-297 (Mar. 1, 2003).

Wierzbicki, *Expert Opinion on Emerging Drugs*, 8(2): 365-376 (2003).

U.S. Appl. No. 10/802,220, filed Mar. 17, 2004, Sunami et al.

U.S. Appl. No. 10/825,531, filed Apr. 15, 2004, Shinkai et al.

U.S. Appl. No. 10/835,916, filed Apr. 30, 2004, Urata et al.

de Grooth et al., *Circulation*, 105, 2159-2165 (May 7, 2002).

Kato et al., *J. Biol. Chem.*, 264, 4082-4087 (Mar. 5, 1989).

Kobayashi et al., *Atherosclerosis*, 162, 131-135 (2002).

Okamoto et al., *Nature*, 406, 203-207 (Jul. 13, 2000).

Shimada et al., *J. Chromatogr. B*, 659, 227-241 (Sep. 23, 1994).

Shinkai et al., *J. Med. Chem.*, 43, 3566-3572 (Sep. 21, 2000).

Tollefson et al., *Methods Enzymol.*, 129, 797-816 (1986).

U.S. Code of Federal Regulations, Title 21, Section 320.1 (2001 ed.).

Welling, *Clin. Pharmacokinet.*, 9 (1), 404-34 (Jan./Feb. 1984).

* cited by examiner

METHOD FOR INCREASING THE BIOAVAILABILITY OF THE ACTIVE FORM OF S-[2-([[1-(2-ETHYLBUTYL)CYCLO-HEXYL]CARBONYL]AMINO) PHENYL] 2-METHYLPROPANETHIOATE

CROSS-REFERENCE TO RELATED APPLICATIONS

This patent application claims the benefit of U.S. Provisional Patent Application No. 60/455,293, filed Mar. 17, 2003; 60/460,521, filed Apr. 4, 2003; and 60/477,202, filed Jun. 10, 2003.

FIELD OF THE INVENTION

This invention is directed to methods for the treatment or prophylaxis of cardiovascular disorders.

BACKGROUND OF THE INVENTION

Hyperlipidemic conditions associated with elevated concentrations of total cholesterol and low-density lipoprotein (LDL) cholesterol are major risk factors for coronary heart disease, and atherosclerosis in particular. Additionally, numerous studies have demonstrated that a low plasma concentration of high-density lipoprotein (HDL) cholesterol is a powerful risk factor for the development of atherosclerosis.

Cholesteryl ester transfer protein (CETP) is a plasma protein that facilitates the movement of cholesteryl esters and triglycerides between various lipoproteins in the blood. The movement of cholesteryl ester from HDL to LDL by CETP has the effect of lowering HDL cholesterol and increasing LDL cholesterol. Inhibition of CETP activity has been shown to effectively modify plasmid HDL/LDL ratios by elevating plasma HDL cholesterol and lowering plasma LDL cholesterol.

S-[2-([[1-(2-ethylbutyl)cyclohexyl]carbonyl]amino)phenyl]2-methylpropanethioate has been shown to be an inhibitor of CETP activity in humans (de Grooth et al., *Circulation*, 105, 2159-2165 (2002)) and rabbits (Shinkai et al., *J. Med. Chem.*, 43, 3566-3572 (2000); Kobayahi et al., *Atherosclerosis*, 162, 131-135 (2002); and Okamoto et al., *Nature*, 406(13), 203-207 (2000)). S-[2-([[1-(2-ethylbutyl)cyclohexyl]carbonyl]amino)phenyl]2-methylpropanethioate has been shown to increase plasma HDL cholesterol in humans (de Grooth et al., supra) and in rabbits (Shinkai et al., supra; Kobayashi et al., supra; Okamoto et al., supra). Moreover, S-[2-([[1-(2-ethylbutyl)cyclohexyl]carbonyl]amino)phenyl]2-methylpropanethioate has been shown to decrease LDL cholesterol in humans (de Grooth et al., supra) and rabbits (Okamoto et al., supra). Additionally, S-[2-([[1-(2-ethylbutyl)cyclohexyl]carbonyl]amino)phenyl]2-methylpropanethioate inhibits the progression of atherosclerosis in rabbits (Okamoto et al., supra). S-[2-([[1-(2-ethylbutyl)cyclohexyl]carbonyl]amino)phenyl]2-methylpropanethioate, as well as methods of making and using the compound, are described in U.S. Pat. No. 6,426,365.

It would be desirable to increase the bioavailability of the active form of S-[2-([[1-(2-ethylbutyl)cyclohexyl]carbonyl]amino)phenyl]2-methylpropanethioate to increase the extent of the therapeutic effect on the user. There remains a need for a method of doing so, for example, a method of treating cardiovascular disorders using S-[2-([[1-(2-ethylbutyl)cyclohexyl]carbonyl]amino)phenyl]2-methylpropanethioate that has increased bioavailability of its active form and, thus, improved efficacy following oral administration to patients. This invention provides such a method, as well as a kit comprising a pharmaceutical composition comprising a therapeutically effective amount of S-[2-([[1-(2-ethylbutyl)cyclohexyl]carbonyl]amino)phenyl]2-methylpropanethioate and a pharmaceutically acceptable carrier, prescribing information, and a container, wherein the prescribing information includes advice to a patient regarding administration of the drug to improve bioavailability. These and other advantages of the invention, as well as additional inventive features, will be apparent from the description of the invention provided herein.

BRIEF SUMMARY OF THE INVENTION

The invention provides a method of increasing the bioavailability of the active form of S-[2-([[1-(2-ethylbutyl)cyclohexyl]carbonyl]amino)phenyl]2-methylpropanethioate in a patient receiving S-[2-([[1-(2-ethylbutyl)cyclohexyl]carbonyl]amino)phenyl]2-methylpropanethioate therapy wherein S-[2-([[1-(2-ethylbutyl)cyclohexyl]carbonyl]amino)phenyl]2-methylpropanethioate is contained in a pharmaceutical composition, which method comprises orally administering a therapeutically effective amount of the drug to the patient with food. The increased bioavailability of the active form can be evidenced by an increase in the maximum plasma concentration of the active form.

The invention also provides a method of increasing the extent of absorption of that active form of S-[2-([[1-(2-ethylbutyl)cyclohexyl]carbonyl]amino)phenyl]2-methylpropanethioate as measured by the concentration of the active form attained in the blood stream over time of a patient receiving the drug in an oral dosage form. This method comprises orally administering a therapeutically effective amount of S-[2-([[1-(2-ethylbutyl)cyclohexyl]carbonyl]amino)phenyl]2-methylpropanethioate to the patient with food.

The invention further provides a method for decreasing the activity of cholesteryl ester transfer protein (CETP) in a patient. The method comprises orally administering a therapeutically effective amount of S-[2-([[1-(2-ethylbutyl)cyclohexyl]carbonyl]amino)phenyl]2-methylpropanethioate to the patient with food.

The invention additionally provides a method for the treatment or prophylaxis of a cardiovascular disorder in a patient. The method comprises orally administering S-[2-([[1-(2-ethylbutyl)cyclohexyl]carbonyl]amino)phenyl]2-methylpropanethioate to the patient with food.

Moreover, the invention provides a kit comprising a pharmaceutical composition comprising a therapeutically effective amount of S-[2-([[1-(2-ethylbutyl)cyclohexyl]carbonyl]amino)phenyl]2-methylpropanethioate and a pharmaceutically acceptable carrier, prescribing information, and a container. The prescribing information includes advice to a patient regarding the administration of S-[2-([[1-(2-ethylbutyl)cyclohexyl]carbonyl]amino)phenyl]2-methylpropanethioate with food.

DETAILED DESCRIPTION OF THE INVENTION

The invention is directed to methods for improving the effectiveness of the administration of S-[2-([[1-(2-ethylbutyl)cyclohexyl]carbonyl]amino)phenyl]2-methylpropanethioate (herein referred to as Compound I) and/or for the treatment or prophylaxis of certain cardiovascular disorders. These disorders include, but are not limited to, cardiovascular disease, coronary heart disease, coronary artery disease, hypoalphalipoproteinemia (low levels of HDL cholesterol), hypercholesterolemia, and atherosclerosis. Additional disorders that may be treated or prevented by the inventive methods include, but are not limited to, hyperlipidemia, hypertension, hypertriglyceridemia, and hyperlipidoproteinemia.

Compound I has the following structural formula:

Pharmacokinetic studies have not previously been conducted to evaluate the effect of food on the pharmacokinetics of the active form of Compound I. In general, food has a variable effect on the bioavailability of an active agent. Drug-food interactions may result in reduced, delayed, or increased systemic drug availability. See, e.g., Welling, *Clin. Pharmacokinet.*, 9(5), 404-34 (1984).

It has been discovered that Compound I can be administered to patients in a regimen that increases the therapeutic effectiveness of Compound I to such patients. Advantageously, when orally administered with food, Compound I exhibits increased bioavailability of the active form of Compound I in patients.

Accordingly, the invention provides a method of increasing the bioavailability of the active form of Compound I in a patient comprising administering to the patient a therapeutically effective amount of Compound I with food.

As used herein, the term "bioavailability" generally means the rate and extent to which the active ingredient, or active form thereof, is absorbed from a drug product and becomes available at the site of action. See U.S. Code of Federal Regulations, Title 21, Part 320.1 (2001 ed.). For oral dosage forms, bioavailability relates to the processes by which the active ingredient is released from the oral dosage form, e.g., a tablet, converted to the active form (if the active ingredient is not already the active form), and moved to the site of action, e.g., absorbed into the systemic circulation.

While not wishing to be bound by any particular theory, it is hypothesized that within the body of a patient, Compound I is hydrolyzed in plasma, the liver, and/or the small intestine to form S-[2([[1-(2-ethylbutyl)cyclohexyl]carbonyl]amino)phenyl]thiol (herein referred to as Compound II). It is known that low molecular weight thiol components (i.e., R-SH), such as cysteine and glutathione, and high molecular weight thiol components (i.e., Prot-SH), such as peptides and proteins (e.g., enzymes and cell membranes), exist in the body as mixed disulfides containing an oxidized disulfide bond (S—S bond) between or within the molecule (see, e.g., Shimada et al., *J. Chromatogr. B*, 659, 227 (1994)). Therefore, it is hypothesized that within the body of a patient, Compound II is conjugated with low or high molecular weight thiols to yield mixed disulfides or to yield dimers of Compound II. Since these forms are in an oxidation-reduction equilibrium with each other via Compound II, all of these forms, as well as Compound II, are collectively, but not exclusively, considered and referred to hereafter as the active form of Compound I. The following scheme depicts the above-described hypothesis.

Compound IV
(dimer)

Compound II

Compound V
(with high molecular
weight thiol component)

While the administration of Compound I is a particularly preferred embodiment of the invention, the invention also contemplates the administration of other compounds that will yield the active form of Compound I, i.e., other prodrugs of the active form of Compound I. Such prodrugs, for example, can be compounds that have different mercapto-protecting groups, but that still result in the formation of the active form of Compound I (e.g., Compound II) in the body of a patient (i.e., in vivo). The term "mercapto-protecting groups" refers to commonly used mercapto-protecting groups (e.g., as described in Wolman, The Chemistry of the Thiol Group, D. Patai, Ed., Wiley-Interscience, New York, 1974). Any organic residues that can be dissociated in vivo may be used without particular restriction. Examples of particularly suitable mercapto-protecting groups are described in U.S. Pat. No. 6,426,365. The invention further contemplates the administration of Compound I' (wherein R' signifies an organic residue other than an isopropyl group) so as to yield the active form of Compound I.

Compound I'

In addition, Compounds III, IV, and V (wherein R signifies an organic residue and Prot signifies a peptide or protein), which are believed to be in equilibrium with Compound II in vivo, similarly can be directly administered to the patient.

As used herein, the term "with food" is defined to mean, in general, the condition of having consumed food during the period between from about 1 hour prior to the administration of Compound I to about 2 hours after the administration of Compound I. Preferably, the food is a solid food with sufficient bulk and fat content that it is not rapidly dissolved and absorbed in the stomach. More preferably, the food is a meal, such as breakfast, lunch, or dinner.

Advantageously, Compound I is administered any time of day with food. The food can be consumed at any time during the period between from about 1 hour prior to the administration of Compound I to about 2 hours after the administration of Compound I. For example, the food can be consumed within the time period of about 1 hour, about 45 minutes, about 30 minutes, about 15 minutes, about 10 minutes, or about 5 minutes prior to the administration of Compound I. Similarly, the food can be consumed within the time period of about 5 minutes, about 10 minutes, about 15 minutes, about 30 minutes, about 45 minutes, about 1 hour, about 1.25 hours, about 1.5 hours, about 1.75 hours, or about 2 hours after the administration of Compound I. More preferably, the administration of Compound I to the patient is immediately after the consumption of food (e.g. within about 1 minute after food consumption) up to about 1 hour after food consumption. Ideally, Compound I is administered at substantially the same time as the consumption of the food.

The terms "without food" or "fasted" are defined to mean the condition of not having consumed food within the time period of about 1 hour prior to the administration of Compound I to about 2 hours after the administration of Compound I.

The term "patient" refers to a human patient.

The methods of the invention are directed to the administration of a therapeutically acceptable amount of Compound I or a prodrug of the active form of Compound I, e.g., a prodrug of Compound II. In general, a suitable dose of a therapeutically effective amount of Compound I for administration to a patient will be between approximately 100 mg to about 1800 mg per day. A suitable dose is preferably about 300 mg to about 900 mg per day. A preferred dose is about 600 mg per day.

If desired, the effective daily dose of Compound I may be administered as two, three, four, five, six, or more sub-doses administered separately at appropriate intervals throughout the day, optionally, in unit dosage forms. Each such sub-dose contains a therapeutically effective amount of Compound I. In accordance with the inventive method, Compound I may be administered with food at multiple times per day or, alternatively, once per day. When administered at multiple times throughout the day, each individual dose contains a therapeutically effective amount of Compound I. In a preferred embodiment of the invention, Compound I is administered with food once per day.

As used herein, the term "unit dosage form" is defined to refer to the form in which Compound I is administered to the patient. Specifically, the unit dosage form can be, for example, a pill, capsule, or tablet. Preferably, the unit dosage form is a tablet. The typical amount of Compound I in a unit dosage form useful in the invention is about 100 mg to about 1800 mg, preferably about 100 mg to about 900 mg (e.g., about 100 mg to about 300 mg). In a preferred embodiment of the invention, the unit dosage form comprises about 300 mg of Compound I and is in the form of a tablet. Preferably, two or three tablets, each of which comprises about 300 mg of Compound I, are administered to the patient once per day (i.e., a total dose per day of about 600 mg or about 900 mg, respectively).

The increased bioavailability of the active form of Compound I to a patient receiving Compound I therapy can be evidenced in any suitable manner. Desirably, the oral administration of Compound I with food results in an increased bioavailability of the active form of Compound I as evidenced by an increase in the maximum plasma concentration of the active form of Compound I as compared to the administration of Compound I without food.

Compound I desirably is provided to a patient in a container associated with prescribing information that advises the patient to orally administer Compound I with food and desirably also explains that doing so will increase the bioavailability of the active form of Compound I. Compound I preferably is provided to a patient in a container associated with prescribing information that advises the patient that the administration of the dose of Compound I in a pharmaceutical composition with food results in an increase in the extent of absorption of the active form of Compound I as reflected by an increase in the maximum plasma concentration of the active form of Compound I as compared to the administration of the drug under fasted conditions.

The invention also provides a method of increasing the extent of absorption of the active form of Compound I as measured by the active form concentration attained in the blood stream over time in a patient in need of a therapeutic effect thereof. This method comprises orally administering to a patient a therapeutically effective amount of Compound I in a pharmaceutical composition with food. The active form concentration in the blood stream is measured as the plasma concentration (μg/mL) of the active form of Compound I. Pharmacokinetic parameters involved in determining the plasma concentration include the maximum observed plasma concentration ($C_{max}$), area under the plasma concentration time curve (AUC) from time zero up to the last quantifiable concentration ($AUC_{0-tz}$), and AUC from time zero to infinity ($AUC_{0-\infty}$). Administering Compound I to a patient with food increases the bioavailability of the active form as measured by increased values of one or more (and desirably all) of the aforesaid pharmacokinetic parameters, when compared to administration of the drug under fasted conditions.

The invention further provides a method for decreasing the activity of cholesteryl ester transfer protein (CETP) in a patient, which comprises orally administering a therapeutically effective amount of Compound I to the patient with food. The decrease in CETP activity is greater following administration of Compound I with food versus under fasted conditions.

Additionally, the invention provides a method for the treatment or prophylaxis of a cardiovascular disorder in a patient comprising administering Compound I to the patient, which comprises orally administering a therapeutically effective amount of Compound I to the patient with food. These disorders include, but are not limited to, cardiovascular disease, coronary heart disease, coronary artery disease, hypoalphalipoproteinemia (low levels of HDL cholesterol), hypercholesterolemia, and atherosclerosis. Additional disorders which may be treated or prevented by the inventive method include, but are not limited to, hyperlipidemia, hypertension, hypertriglyceridemia, and hyperlipidoproteinemia.

Compound I may be administered for therapy to a patient in any conventional manner. While it is possible for Compound I to be administered as the raw chemical, it is preferably administered as a pharmaceutical composition. Such pharmaceutical compositions comprise Compound I with one or more pharmaceutically acceptable carriers or excipients and optionally other therapeutic agents and/or components. The carriers or excipients must be acceptable in the sense of being compatible with the other ingredients and not deleterious to the recipient thereof. Examples of carriers or excipients for oral administration include cornstarch, lactose, magnesium stearate, talc, microcrystalline cellulose, stearic acid, povidone, crospovidone, dibasic calcium phosphate, sodium starch glycolate, hydroxypropyl cellulose (e.g., low substituted hydroxypropyl cellulose), hydroxypropylmethyl cellulose (e.g., hydroxypropylmethyl cellulose 2910), and sodium lauryl sulfate.

The pharmaceutical compositions can be prepared by any suitable method, such as those methods well known in the art of pharmacy, for example, methods such as those described in Gennaro et al., Remington's Pharmaceutical Sciences (18th ed., Mack Publishing Co., 1990), especially Part 8: Pharmaceutical Preparations and their Manufacture. Such methods include the step of bringing into association Compound I with the carrier or excipient and optionally one or more accessory ingredients. Such accessory ingredients include those conventional in the art, such as, fillers, binders, diluents, disintegrants, lubricants, colorants, flavoring agents, and wetting agents.

The pharmaceutical compositions can provide controlled, slow release, or sustained release of the Compound I over a predetermined period of time. The controlled, slow release, or sustained release of the therapeutic compound can provide for a concentration of the active form of Compound I to be maintained in the bloodstream of the patient for a longer period of time than with conventional formulations. Such pharmaceutical compositions include coated tablets, pellets, and capsules, as well as dispersions of the therapeutic compound in a medium that is insoluble in physiologic fluids or where the release of the therapeutic compound follows degradation of the pharmaceutical composition due to mechanical, chemical, or enzymatic activity.

The pharmaceutical composition in the context of the invention can be, for example, in the form of a pill, capsule, or tablet, each containing a predetermined amount of Compound I and preferably coated for ease of swallowing, in the form of a powder or granules, or in the form of a solution or suspension. Preferably, the pharmaceutical composition is in the form of a tablet comprising Compound I (or a prodrug of the active form of Compound I) and the components of the tablet utilized and described in the Examples herein. For oral administration, fine powders or granules may contain diluting, dispersing, and or surface active agents and may be present, for example, in water or in a syrup, in capsules or sachets in the dry state, or in a nonaqueous solution or suspension wherein suspending agents may be included, or in tablets wherein binders and lubricants may be included. Components such as sweeteners, flavoring agents, preservatives (e.g., antimicrobial preservatives), suspending agents, thickening agents, and/or emulsifying agents also may be present in the pharmaceutical composition. When administered in the form of a liquid solution or suspension, the formulation can contain Compound I and purified water. Optional components in the liquid solution or suspension include suitable sweeteners, flavoring agents, preservatives (e.g., antimicrobial preservatives), buffering agents, solvents, and mixtures thereof. A component of the formulation may serve more than one function. For example, a suitable buffering agent also may act as a flavoring agent as well as a sweetener.

Suitable sweeteners include, for example, saccharin sodium, sucrose, and mannitol. A mixture of two or more sweeteners optionally may be used. The sweetener or mixtures thereof are typically present in an amount of from about 0.001% to about 70% by weight of the total composition. Suitable flavoring agents may be present in the pharmaceutical composition to provide a cherry flavor, cotton candy flavor, or other suitable flavor to make the pharmaceutical composition easier for a patient to ingest. The flavoring agent or mixtures thereof are typically present in an amount of about 0.0001% to about 5% by weight of the total composition.

Suitable preservatives include, for example, methylparaben, propylparaben, sodium benzoate, and benzalkoniyum chloride. A mixture of two or more preservatives optionally may be used. The preservative or mixtures thereof are typically present in an amount of about 0.0001% to about 2% by weight of the total composition.

Suitable buffering agents include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

Suitable solvents for a liquid solution or suspension include, for example, sorbital, glycerin, propylene glycol, and water. A mixture of two or more solvents optionally may be used. The solvent or solvent system is typically present in an amount of about 1% to about 90% by weight of the total composition.

Oral delivery methods are often limited by chemical and physical barriers imposed by the body, such as the varying pH in the gastrointestinal tract, exposure to enzymes, and the impermeability of the gastrointestinal membranes. The oral administration of the pharmaceutical composition may also include the co-administration of adjuvants. For example, nonionic surfactants such as polyoxyethylene oleyl ether and n-hexadecyl polyethylene ether can be administered with or incorporated into the pharmaceutical composition to artificially increase the permeability of the intestinal walls. Enzymatic inhibitors also can be administered with or incorporated into the pharmaceutical composition.

Moreover, the invention provides a kit comprising a pharmaceutical composition comprising a therapeutically effective amount of Compound I and a pharmaceutically acceptable carrier, prescribing information, and a container. The prescribing information can be prescribing information conforming to the methods of the invention and/or as otherwise discussed herein. The prescribing information preferably includes advice to a patient regarding the administration of Compound I with food, especially to improve the bioavailability of the active form of Compound I.

The following examples further illustrate the invention but, of course, should not be construed as in any way limiting its scope.

EXAMPLE 1

The effect of food on Compound I absorption in patients was identified in a study designed to compare the bioavailability of 900 mg of Compound I orally administered to Caucasian male volunteers with and without food.

For this study each of six subjects received Compound I at a dose level of 900 mg in each of two treatment periods, once with food (after a standard breakfast) and once in the fasted state. There was a minimum of 7 days between each treatment period. This interval of 7 days between treatments was considered appropriate for eliminating any within-subject carryover effects.

The subjects received 900 mg of Compound I by administration of 3 tablets of 300 mg each. The uncoated white tablets were prepared using standard tableting procedures. The tablets comprised 300 mg of Compound 1,18 mg of hydroxypropylmethyl cellulose 2910 as a binder, 18 mg of talc and 1.2 mg of magnesium stearate as lubricants, and 119.8 mg of crospovidone and 90 mg of low-substituted hydroxypropyl cellulose as disintegrants.

Treatments were administered orally with 150 mL water while standing. Subjects were not allowed to lie supine for 2 hours after dose administration, except for study procedures.

Doses were administered at similar times for each subject in each treatment period. Dosing commenced at approximately 08:30 hours. All subjects fasted from food and fluids (with the exception of water) from 22:00 hours on the day prior to dosing (Day—1) until breakfast on Day 1 (for subjects receiving Compound I in the fed state (i.e., with food)) or lunch-time on Day 1 (for subjects Compound I in the fasted state), and during the evening prior to the post-study visit until laboratory safety evaluations had been performed on the following day. Water could be consumed at any time during the study, with the exception of the period up to 2 hours post-dose, when no fluids were permitted.

When subjects were administered Compound I in the fed state, they received a standard breakfast about 45 minutes prior to dosing. The meal was eaten at a steady rate over a 15 minute period so that the meal was completed 30 minutes before dosing. The standard breakfast consisted of the following:

200 mL orange juice

Two packets of cereal (approximately 60 g)

Two slices of wholemeal toast 10 g low fat spread (one packet)

20 g jam (one packet)

242 mL full fat milk (approximately 250 g)

| Total energy content: | 711 Kcal |
|---|---|
| Total fat content: | 15.72 g (19.9% of total calories) |
| Total protein: | 20.82 g (11.7% total calories) |

Blood samples for pharmacokinetic analysis were taken immediately prior to dosing and at the following times after dosing: 1, 2, 4, 6, 7, 10, 12, 24, and 36 hours post-dose.

The following pharmacokinetic parameters were calculated for the two profiles (fed and fasted conditions) and are defined as follows:

| | |
|---|---|
| $t_{max}$ | Time of maximum observed plasma concentration; |
| $C_{max}$ | Maximum observed plasma concentration; |
| $t_{1/2}$ | Half-life of plasma concentration of the active form of Compound I |

-continued

AUC$_{0-tz}$  Area under the plasma concentration-time curve (AUC) from time zero up to the last quantifiable concentration (AUC (0 – t$_z$)); and AUC$_{0-\infty}$  AUC from time zero to infinity Pharmacokinetic parameters were log-transformed by analysis and assessed using SAS® Least Square Means derived from a three-way analysis of variance (ANOVA) fitting effects for subject, treatment, and period. Treatment comparisons were made by calculating the difference and 95% confidence intervals (CIs) of the difference of the log SAS® Least Square Means between parameters for the respective treatments. The differences and CIs of the differences were back-transformed for reporting purposes.

The plasma concentration of the active form of Compound I was determined by the following assay. Plasma samples were isolated from patients treated with Compound I. The plasma samples were treated with sodium hydroxide (Wako Pure Chemical Industries, Ltd.) to convert active forms of Compound I in the plasma to the thiol form (i.e., Compound II). The plasma sample next was treated with dithiothreitol (DTT) (Wako Pure Chemical Industries, Ltd.) to prevent the oxidation of thiol groups (i.e., to maintain thiol groups in a reduced state). N-ethylmaleimide (NEM) (Wako Pure Chemical Industries, Ltd.) was added to stabilize the thiol form (i.e., Compound II) by, it is believed, blocking the free sulfhydryl group by the derivatization to an NEM-adduct. The sample then was analyzed using High Performance Liquid Chromatography (HPLC). Finally, the results of the HPLC analysis of the plasma sample were compared to a known standard to determine the plasma concentration of the active form of Compound I. The standard of known concentration was prepared essentially as described above, with the exception that human plasma was isolated from humans who were not treated with Compound I. These "blank plasma" samples were combined with a known amount of Compound I.

The mean test results for plasma pharmacokinetic parameters, AUC$_{0-\infty}$ (μg h/mL), AUC$_{0-tz}$ (μg h/mL), C$_{max}$ (μg/mL), t$_{1/2}$ (h), and t$_{max}$ (h), of the active form of Compound I are summarized in Table 1.

TABLE 1

Plasma Pharmacokinetic Parameters of the Active Form of S-[2-([[1-(2-ethylbutyl)cyclohexyl]carbonyl]amino)phenyl] 2-methyl-propanethioate

| Parameter | Treatment Protocol | | Ratio |
|---|---|---|---|
| | Fasted | Fed | (Fed:Fasted) |
| AUC (0 – t$_z$)* (μg h/mL) | 6.21 (46.9) | 10.2 (19.0) | 1.65 |
| AUC (0 – ∞)* (μg h/mL) | 7.97 (46.7) | 12.5 (17.4) | 1.57 |
| C$_{max}$* (μg/mL) | 0.423 (37.1) | 0.955 (26.1) | 2.26 |
| t$_{max}$ (h)+ | 5.00 (2.00-6.00) | 4.00 (2.00-6.00) | NA |

TABLE 1-continued

Plasma Pharmacokinetic Parameters of the Active Form of S-[2-([[1-(2-ethylbutyl)cyclohexyl]carbonyl]amino)phenyl] 2-methyl-propanethioate

| Parameter | Treatment Protocol | | Ratio |
|---|---|---|---|
| | Fasted | Fed | (Fed:Fasted) |
| t$_{1/2}$ (h)‡ | 16.5 (14.1-22.4) | 15.4 (12.6-18.6) | 0.935 |

*= geometric mean (geometric coefficient of variation %)
+= median (min-max)
NA = not applicable
‡= harmonic mean (min-max)

The absorption of the active form of Compound I was relatively slow, with the time of maximum observed plasma concentration occurring at between 4 and 5 hours after administration of Compound I. As is apparent from Table 1, the time of maximum observed plasma concentration was similar after administration of Compound I with and without food. Additionally, the half life of the active form of Compound I was determined to be similar after administration of the drug with and without food.

Figure 1:
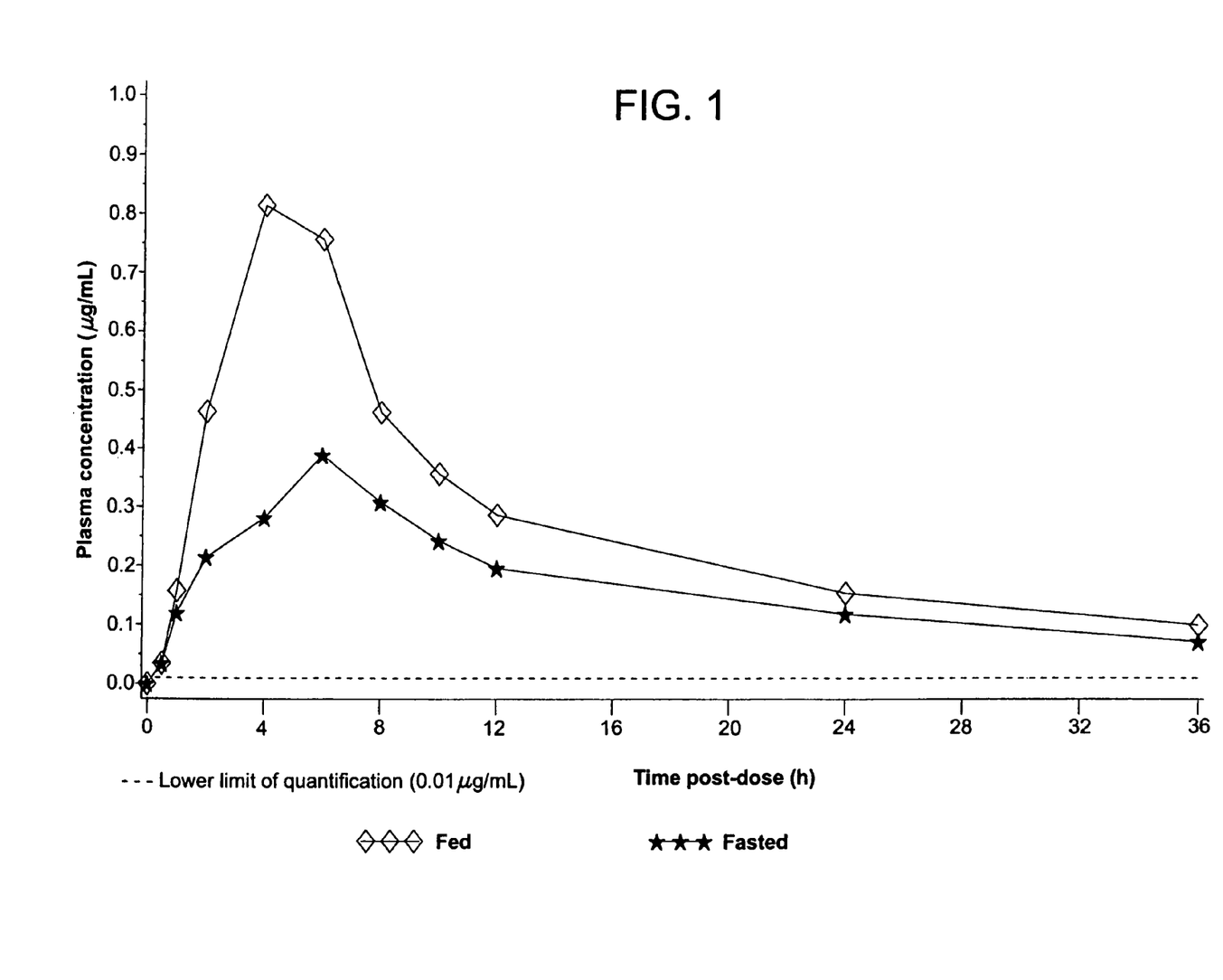
FIG. 1 is a linear plot of the geometric mean plasma concentrations (μg/mL) of the active form of S-[2-([[1-(2-ethylbutyl)cyclohexyl]carbonyl]amino)phenyl]2-methylpropanethioate over 36 hours in Caucasian male patients, who were orally administered 900 mg of S-[2-([[1-(2-ethylbutyl)cyclohexyl]carbonyl]amino)phenyl]2-methylpropanethioate with food or without food.
Figure 2:
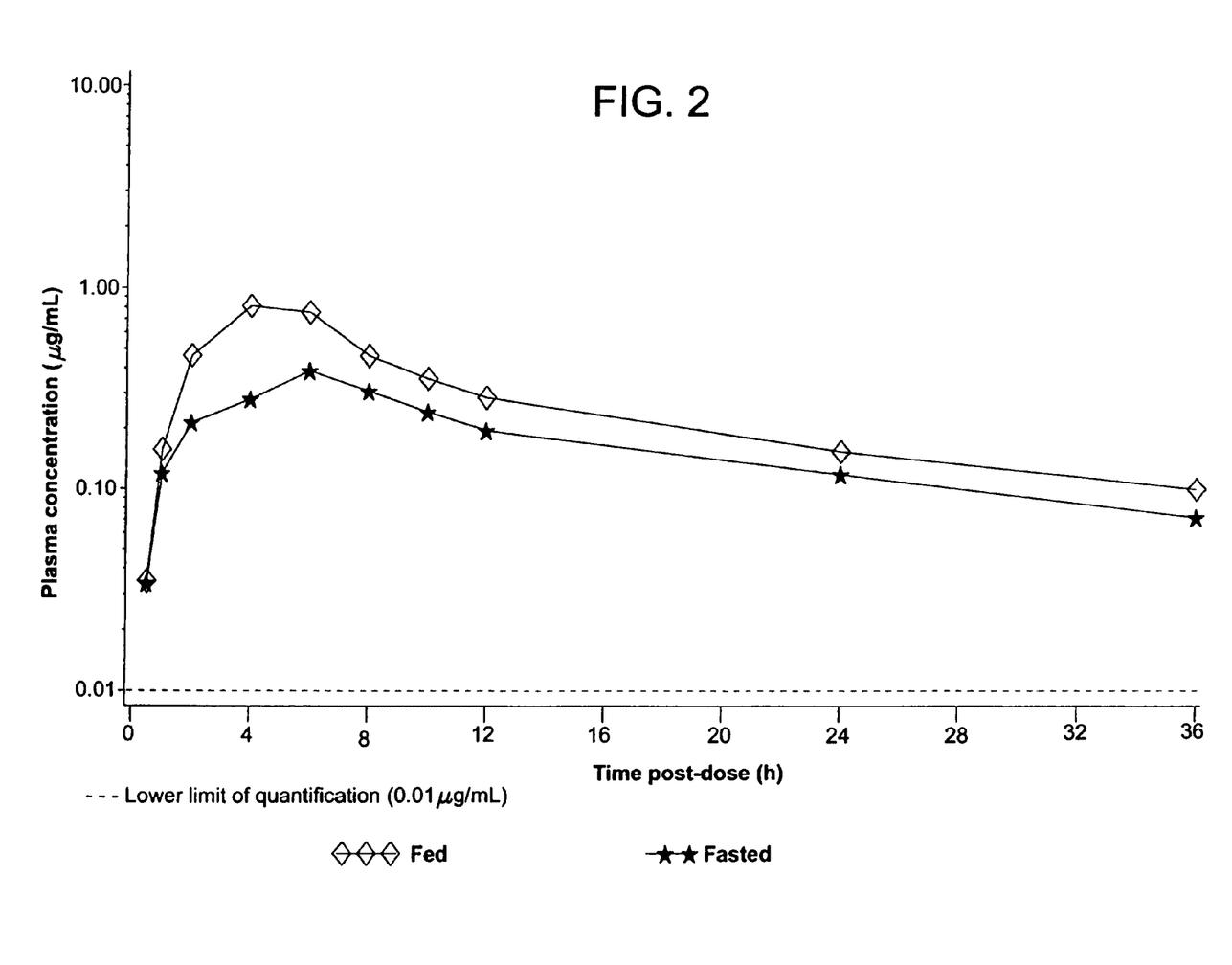
FIG. 2 is a semi-logarithmic plot of the geometric mean plasma concentrations (μg/mL) of the active form of S-[2-([[1-(2-ethylbutyl)cyclohexyl]carbonyl]amino)phenyl]2-methylpropanethioate over 36 hours in Caucasian male patients, who were orally administered 900 mg of S-[2-([[1-(2-ethylbutyl)cyclohexyl]carbonyl]amino)phenyl]2-methylpropanethioate with food or without food.

Several of the pharmacokinetic parameters, however, were affected by the administration of Compound I with food. These include AUC$_{0-tz}$, AUC$_{0-\infty}$, and C$_{max}$, which were 65%, 57%, and 126% higher, respectively, when Compound I was administered with food as compared with the administration of Compound I in the fasted state. These increases are noticeably apparent when the geometric mean plasma concentrations of the active form of Compound I were plotted in linear form in FIG. 1 and plotted in semi-logarithmic form in FIG. 2.

The observed increases in pharmacokinetic parameters when Compound I is administered with food indicate an increase in the bioavailability of the active form of the drug when compared to administration of the drug under fasted conditions.

EXAMPLE 2

The effect of food on the absorption of the active form of Compound I in Caucasian male patients was identified in a study designed to compare the CETP activity following the oral administration of 900 mg of Compound I with and without food.

Administration, dosing, and sampling schedules were substantially similar to those described in Example 1.

The procedure for determining CETP activity was substantially similar to the procedures described in Tollefson et al., *Methods Enzymol.*, 129, 797-816 (1986), and Kato et al., *J. Biol. Chem.*, 264, 4082-4087 (1989).

Figure 3:
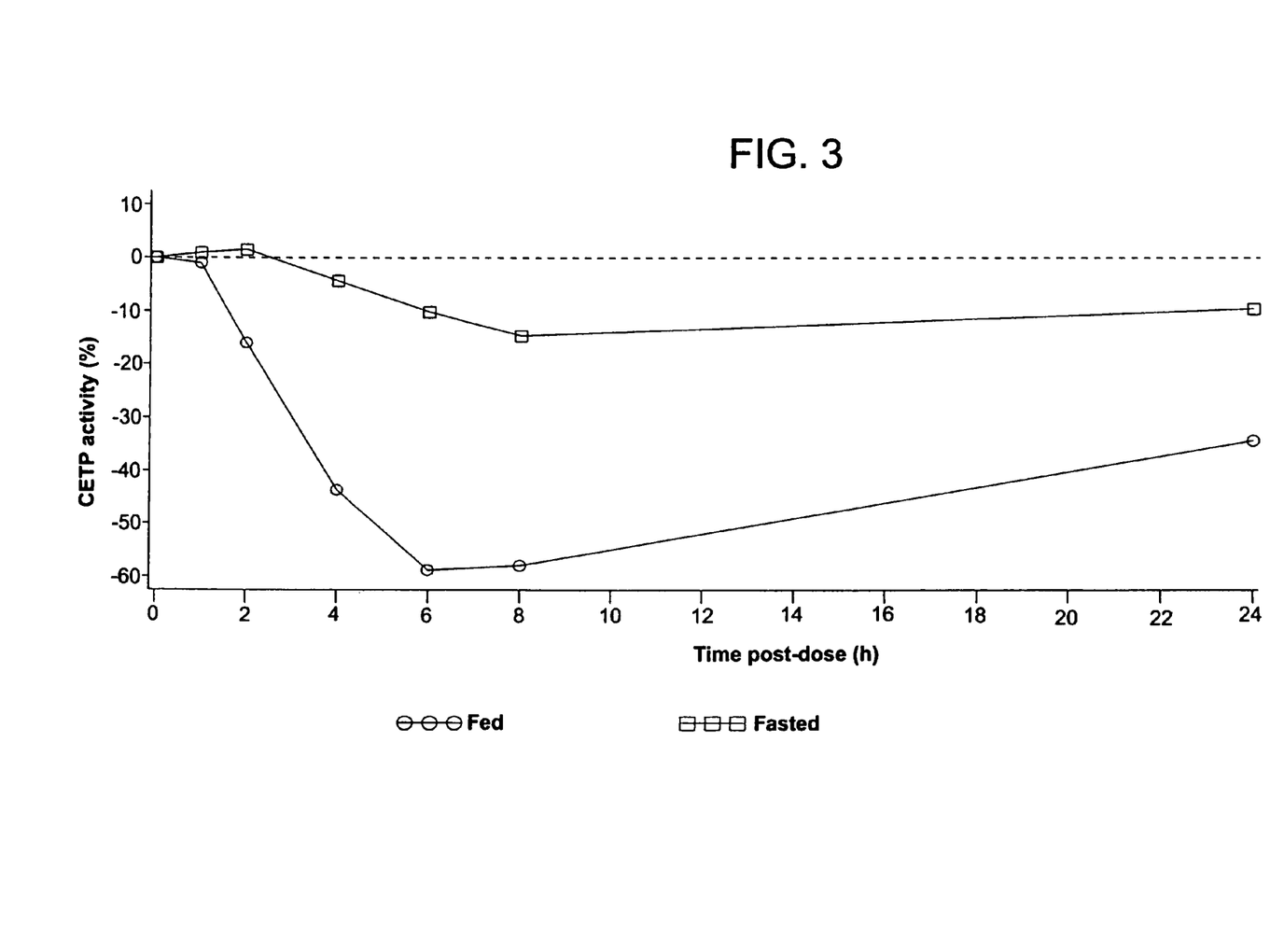
FIG. 3 is plot of the mean changes from baseline (pre-dose) in CETP activity over 24 hours in Caucasian male patients, who were orally administered 900 mg of S-[2-([[1-(2-ethylbutyl)cyclohexyl]carbonyl]amino)phenyl]2-methyl-propanethioate with food or without food.

CETP activity and changes from baseline (pre-dose) were measured, and the resulting data is summarized in Table 2 as percentage change from baseline. The mean changes from baseline (pre-dose) in CETP activity over time are set out in the plot of FIG. 3.

TABLE 2

Mean (S.D.) Changes from Baseline (Pre-dose) in CETP Activity

Percent Changes from Pre-dose (standard deviation)

| Treatment Protocol | Pre-dose | 1 h | 2 h | 4 h | 6 h | 8 h | 24 h | Post-study (all subjects) |
|---|---|---|---|---|---|---|---|---|
| Fed | 96 (17.0) | −1 (2.3) | −16 (13.2) | −44 (14.0) | −59 (11.1) | −58 (11.1) | −34 (7.5) | 96 (17.4) |
| Fasted | 91 (16.0) | 1 (2.2) | 2 (2.4) | −4 (2.2) | −10 (3.1) | −15 (4.7) | −10 (3.8) | |

A clear difference in CETP activity was observed when Compound I was administered with and without food. Inhibition of CETP activity was much more marked in the fed treatment protocol as compared with the fasted treatment protocol. For example, between 4 and 24 hours post-dose, there is a significant decrease in CETP activity in the fed versus the fasted state. Such a decrease in CETP activity indicates increased bioavailability of the active form of the drug when administered with food as compared to administration of the drug without food.

Figure 4:
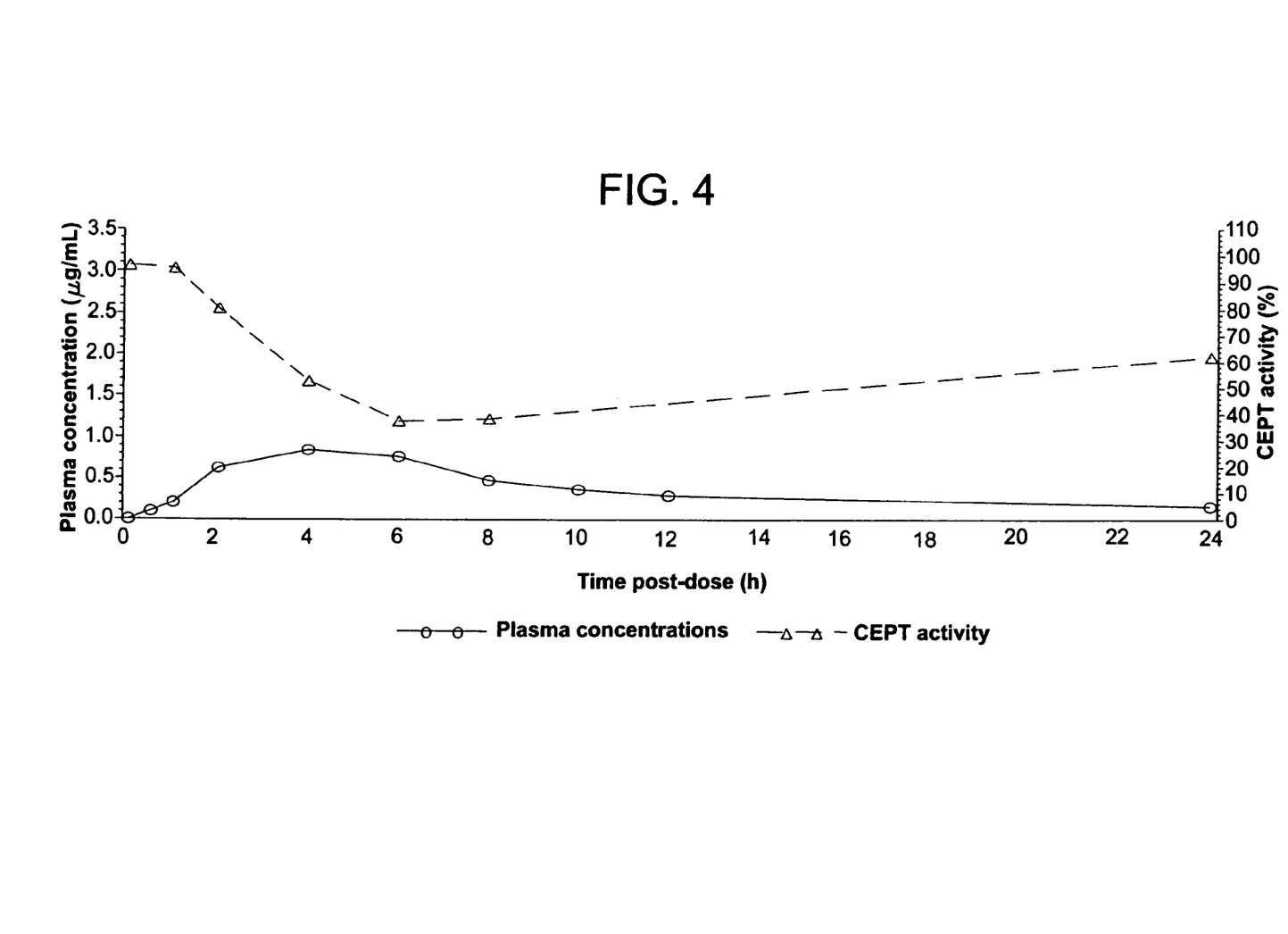
FIG. 4 is a plot of mean CETP activities and mean plasma concentrations of the active form of S-[2-([[1-(2-ethylbutyl)cyclohexyl]carbonyl]amino)phenyl]2-methylpropanethioate over 24 hours in Caucasian male patients following the oral administration of 900 mg of S-[2-([[1-(2-ethylbutyl)cyclohexyl]carbonyl]amino)phenyl]2-methylpropanethioate with food.
Figure 5:
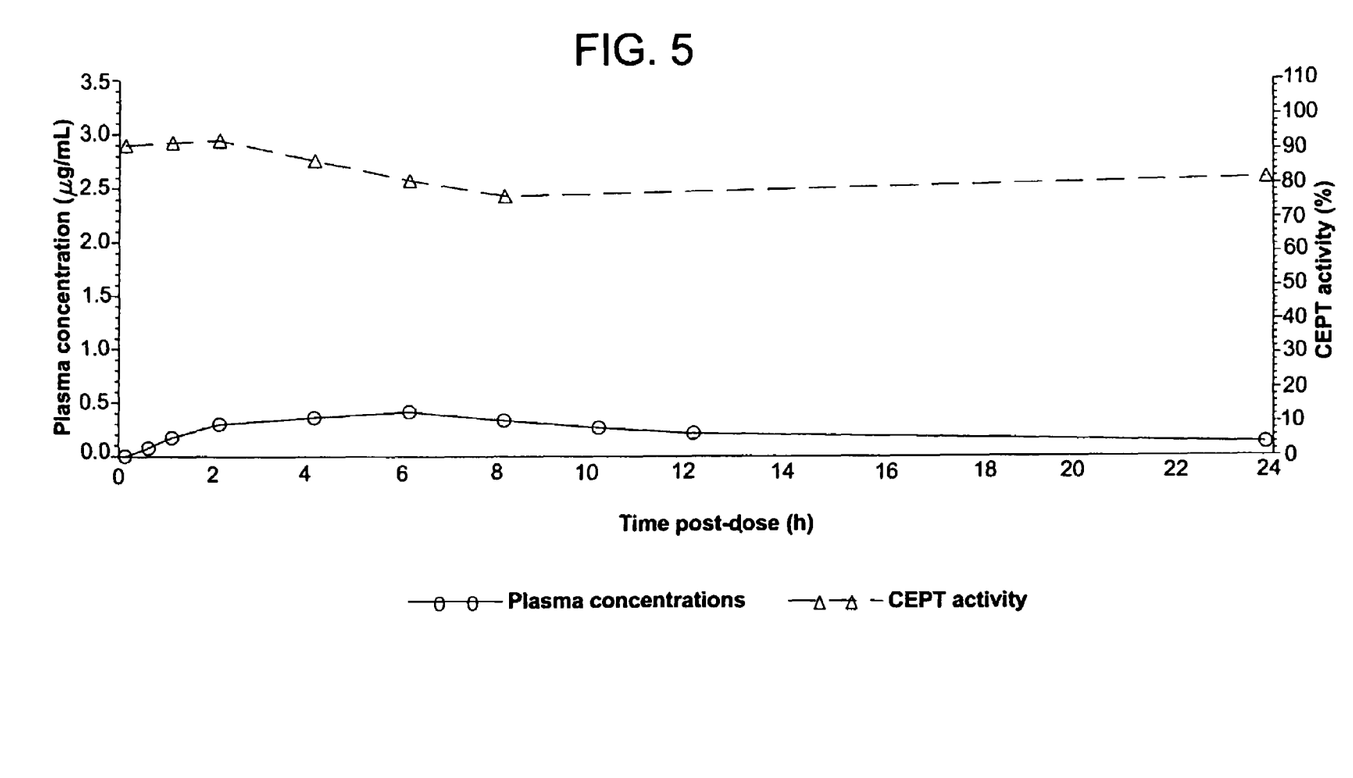
FIG. 5 is a plot of mean CETP activities and mean plasma concentrations of the active form of S-[2-([[1-(2-ethylbutyl)cyclohexyl]carbonyl]amino)phenyl]2-methylpropanethioate over 24 hours in Caucasian male patients following the oral administration of 900 mg of S-[2-([[1-(2-ethylbutyl)cyclohexyl]carbonyl]amino)phenyl]2-methylpropanethioate without food.

The relationships between plasma concentrations of the active form of Compound I and inhibition of CETP activity for the fed and fasted states are illustrated by the plots of FIGS. 4 and 5, respectively. As plasma concentrations of the active form of Compound I increased, the inhibitory effect on CETP increased (i.e., CETP activity decreased).

EXAMPLE 3

In a similar study to that described in Example 2, the effect of food on the absorption of the active form of Compound I in Japanese male patients was identified in a study designed to compare the relative CETP activity following the oral administration of 600 mg of Compound I with and without food.

Administration, dosing, and sampling schedules were commensurate with those described in Examples 1 and 2. However, patients were administered 600 mg (rather than 900 mg) of Compound I with and without food. Patients were administered two tablets of 300 mg each. The tablets were prepared as described in Example 1.

Relative CETP activities (calculated as a percentage of baseline CETP activity) and standard deviations (SD) were measured, and the resulting data is summarized in Table 3.

protocol. For example, between 4 and 24 hours post-dose, there was a significant decrease in CETP activity in the fed versus the fasted state. Specifically, the inhibition of CETP activity following the administration of Compound I with food reached its peak at 6 hours post-administration with 37.6% CETP activity relative to baseline. In contrast, the inhibition of CETP activity following the administration of Compound I without food reached its peak at 8 hours post-administration with 87.8% CETP activity relative to baseline. Such a decrease in the relative CETP activity following the administration of Compound I with food indicates increased bioavailability of the active form of the drug when administered with food as compared to the administration of the drug without food.

EXAMPLE 4

In a similar study to that described in Example 1, the effect of food on the absorption of the active form of Compound I in patients was identified in a study designed to compare the bioavailability of 600 mg of Compound I orally administered to Japanese male volunteers with and without food.

Administration, dosing, and sampling schedules were commensurate with those described in Example 1. However, patients were administered 600 mg (rather than 900 mg) of S-[2-([[1-(2-ethylbutyl)cyclohexyl]carbonyl]amino)phenyl] 2-methylpropanethioate with and without food. Patients were administered two tablets of 300 mg each. The tablets were prepared as described in Example 1.

As observed in Example 1, pharmacokinetics parameters, such as maximum observed plasma concentration ($C_{max}$) and area under the plasma concentration-time curve from time zero to infinity ($AUC_{0-\infty}$), were affected by adminis-

TABLE 3

Relative CETP Activity

CETP Activity Relative to Pre-dose (standard deviation)

| Treatment Protocol | Pre-dose | 1 h | 2 h | 4 h | 6 h | 8 h | 24 h | Post-study |
|---|---|---|---|---|---|---|---|---|
| Fed | 100 (0.0) | 100.4 (1.9) | 87.8 (9.2) | 52.6 (13.4) | 37.6 (6.6) | 39.1 (8.3) | 65.5 (5.7) | 102.9 (7.3) |
| Fasted | 100 (0.0) | 102.1 (3.6) | 99.6 (2.1) | 96.5 (3.1) | 89.5 (2.0) | 87.8 (4.6) | 92.6 (3.0) | 100.4 (2.8) |

A clear difference in CETP relative activity was observed when Compound I was administered with and without food, consistent with the results discussed in Example 2. Inhibition of CETP activity was much more marked in the fed treatment protocol as compared with the fasted treatment tration of Compound I with food. The $C_{max}$ (mean) value after administration of 600 mg of Compound I was 1.029 μg/mL when administered with food and only 0.316 μg/mL when administered without food. The $AUC_{0-\infty}$ (mean) value after administration of 600 mg of Compound I was 10.458

µg h/mL when administered with food and only 5.395 µg h/mL when administered without food. Thus, the $C_{max}$ and $AUC_{0-\infty}$ were about 3 and 2 times higher, respectively, when the patients were administered the drug with food as compared to without food.

The observed increases in the pharmacokinetic parameters when Compound I is administered with food indicate that the active form of the drug is more readily absorbed when administered with food, such as after a meal. Thus, the administration of Compound I with food results in an increase in the bioavailability of the active form of the drug when compared to the administration of the drug under fasted conditions.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of increasing the bioavailability of the active form of S-[2-([[1-(2-ethylbutyl)cyclohexyl]carbonyl]amino)phenyl]2-methylpropanethioate to a patient receiving S-[2-([[1-(2-ethylbutyl)cyclohexyl]carbonyl]amino)phenyl]2-methylpropanethioate therapy comprising orally administering to the patient once per day a therapeutically effective amount of S-[2-([[1-(2-ethylbutyl)cyclohexyl]carbonyl]amino)phenyl]2-methylpropanethioate in a pharmaceutical composition with food, wherein the food is not part of the pharmaceutical composition.

2. The method of claim 1, wherein the therapeutically effective amount is about 100 mg to about 1800 mg.

3. The method of claim 2, wherein the therapeutically effective amount is about 300 mg to about 900 mg.

4. The method of claim 1, wherein the administration to the patient occurs between about 1 hour prior to consuming food to about 2 hours after consuming food.

5. The method of claim 4, wherein the administration to the patient is substantially at the same time as the consumption of the food.

6. The method of claim 4, wherein the administration to the patient is immediately after the consumption of food to up to about 1 hour after the consumption of food.

7. The method of claim 1, wherein the pharmaceutical composition is in a unit dosage form of a tablet.

8. The method of claim 7, wherein the tablet comprises about 100 mg to about 1800 mg of S-[2-([[1-(2-ethylbutyl)cyclohexyl]carbonyl]amino)phenyl]2-methylpropanethioate.

9. The method of claim 8, wherein the tablet comprises about 300 mg of S-[2-([[1-(2-ethylbutyl)cyclohexyl]carbonyl]amino)phenyl]2-methylpropanethioate, and the therapeutically effective amount is about 300 mg to about 900 mg.

10. The method of claim 1, wherein the administration results in an increase in the maximum plasma concentration of the active form of S-[2-([[1-(2-ethylbutyl)cyclohexyl]carbonyl]amino)phenyl]2-methylpropanethioate as compared to the administration of S-[2-([[1-(2-ethylbutyl)cyclohexyl]carbonyl]amino)phenyl]2-methylpropanethioate without food.

11. The method of claim 1, wherein the pharmaceutical composition is provided to a patient in a container associated with prescribing information that advises the patient that the pharmaceutical composition is to be administered with food.

12. The method of claim 11, wherein prescribing information further advises the patient that the administration of S-[2-([[1-(2-ethylbutyl)cyclohexyl]carbonyl]amino)phenyl]2-methylpropanethioate in a pharmaceutical composition with food results in an increase of the maximum plasma concentration of the active form of S-[2-([[1-(2-ethylbutyl)cyclohexyl]carbonyl]amino)phenyl]2-methylpropanethioate as compared to the administration of S-[2-([[1-(2-ethylbutyl)cyclohexyl]carbonyl]amino)phenyl]2-methylpropanethioate under fasted conditions.

13. The method of claim 11, wherein the prescribing information further advises the patient to administer the pharmaceutical composition between about 1 hour prior to consuming food to about 2 hours after consuming food.

14. The method of claim 13, wherein the prescribing information further advises the patient to administer the pharmaceutical composition substantially at the same time as consuming food.

15. The method of claim 13, wherein the prescribing information further advises the patient to administer the pharmaceutical composition immediately after consuming food to up to about 1 hour after consuming food.

16. A method of increasing the extent of absorption of the active form of S-[2-([[1-(2-ethylbutyl)cyclohexyl]carbonyl]amino)phenyl]2-methylpropanethioate as measured by the active form concentration attained in the blood stream over time in a patient in need of a therapeutic effect thereof comprising orally administering to the patient a therapeutically effective amount of S-[2-([[1-(2-ethylbutyl)cyclohexyl]carbonyl]amino)phenyl]2-methylpropanethioate in a pharmaceutical composition with food, wherein the food is not part of the pharmaceutical composition.

17. The method of claim 16, wherein the therapeutically effective amount is about 100 mg to about 1800 mg.

18. The method of claim 17, wherein the therapeutically effective amount is about 300 mg to about 900 mg.

19. The method of claim 16, wherein the administration to the patient occurs between about 1 hour prior to consuming food to about 2 hours after consuming food.

20. The method of claim 19, wherein the administration to the patient is substantially at the same time as the consumption of the food.

21. The method of claim 19, wherein the administration to the patient is immediately after the consumption of food to up to about 1 hour after the consumption of food.

22. The method of claim 16, wherein the pharmaceutical composition is in a unit dosage form of a tablet.

23. The method of claim 22, wherein the tablet comprises about 100 mg to about 1800 mg of S-[2-([[1-(2-ethylbutyl)cyclohexyl]carbonyl]amino)phenyl]2-methylpropanethioate.

24. The method of claim 23, wherein the tablet comprises about 300 mg of S-[2-([[1-(2-ethylbutyl)cyclohexyl]carbonyl]amino)phenyl]2-methylpropanethioate, and the therapeutically effective amount is about 300 mg to about 900 mg.

25. A method for decreasing the activity of cholesteryl ester transfer protein (CETP) in a patient, which comprises orally administering to the patient once per day a therapeutically effective amount of S-[2-([[1-(2-ethylbutyl)cyclohexyl]carbonyl]amino)phenyl]2-methylpropanethioate in a pharmaceutical composition with food wherein the food is not part of the pharmaceutical composition.

26. The method of claim 25, wherein the therapeutically effective amount is about 100 mg to about 1800 mg.

27. The method of claim 26, wherein the therapeutically effective amount is about 300 mg to about 900 mg.

28. The method of claim 25, wherein the administration to the patient occurs between about 1 hour prior to consuming food to about 2 hours after consuming food.

29. The method of claim 28, wherein the administration to the patient is substantially at the same time as the consumption of the food.

30. The method of claim 28, wherein the administration to the patient is immediately after the consumption of food to up to about 1 hour after the consumption of food.

31. The method of claim 25, wherein the pharmaceutical composition is in a unit dosage form of a tablet.

32. The method of claim 31, wherein the tablet comprises about 100 mg to about 1800 mg of S-[2-([[1-(2-ethylbutyl)cyclohexyl]carbonyl]amino)phenyl]2-methylpropanethioate.

33. The method of claim 32, wherein the tablet comprises about 300 mg of S-[2-([[1-(2-ethylbutyl)cyclohexyl]carbonyl]amino)phenyl]2-methylpropanethioate, and the therapeutically effective amount is about 300 mg to about 900 mg.

34. A method for the treatment or prophylaxis of a cardiovascular disorder in a patient, which comprises orally administering to the patient once per day a therapeutically effective amount of S-[2-([[1-(2-ethylbutyl)cyclohexyl]carbonyl]amino)phenyl]2-methylpropanethioate in a pharmaceutical composition with food, wherein the food is not part of the pharmaceutical composition.

35. The method of claim 34, wherein the cardiovascular disorder is selected from the group consisting of cardiovascular disease, coronary heart disease, coronary artery disease, hypoalphalipoproteinemia, hypercholesterolemia, and atherosclerosis.

36. The method of claim 34, wherein the therapeutically effective amount is about 100 mg to about 1800 mg.

37. The method of claim 36, wherein the therapeutically effective amount is about 300 mg to about 900 mg.

38. The method of claim 34, wherein the administration to the patient occurs between about 1 hour prior to consuming food to about 2 hours after consuming food.

39. The method of claim 38, wherein the administration to the patient is substantially at the same time as the consumption of the food.

40. The method of claim 38, wherein the administration to the patient is immediately after the consumption of food to up to about 1 hour after the consumption of food.

41. The method of claim 34, wherein the pharmaceutical composition is in a unit dosage form of a tablet.

42. The method of claim 41, wherein the tablet comprises about 100 mg to about 1800 mg of S-[2-([[1-(2-ethylbutyl)cyclohexyl]carbonyl]amino)phenyl]2-methylpropanethioate.

43. The method of claim 42, wherein the tablet comprises about 300 mg of S-[2-([[1-(2-ethylbutyl)cyclohexyl]carbonyl]amino)phenyl]2-methylpropanethioate, and the therapeutically effective amount is about 300 mg to about 900 mg.

44. A method for increasing plasma high-density lipoprotein (HDL) cholesterol in a patient, which method comprises orally administering to the patient once per day a therapeutically effective amount of S-[2-([[1-(2-ethylbutyl)cyclohexyl]carbonyl]amino)phenyl]2-methylpropanethioate in a pharmaceutical composition with food, wherein the food is not part of the pharmaceutical composition.

45. The method of claim 44, wherein the therapeutically effective amount is about 100 mg to about 1800 mg.

46. The method of claim 45, wherein the therapeutically effective amount is about 300 mg to about 900 mg.

47. The method of claim 44, wherein the administration to the patient occurs between about 1 hour prior to consuming food to about 2 hours after consuming food.

48. The method of claim 47, wherein the administration to the patient is substantially at the same time as the consumption of the food.

49. The method of claim 47, wherein the administration to the patient is immediately after the consumption of food to up to about 1 hour after the consumption of food.

50. The method of claim 44, wherein the pharmaceutical composition is in a unit dosage form of a tablet.

51. The method of claim 50, wherein the tablet comprises about 100 mg to about 1800 mg of S-[2-([[1-(2-ethylbutyl)cyclohexyl]carbonyl]amino)phenyl]2-methylpropanethioate.

52. The method of claim 51, wherein the tablet comprises about 300 mg of S-[2-([[1-(2-ethylbutyl)cyclohexyl]carbonyl]amino)phenyl]2-methylpropanethioate, and the therapeutically effective amount is about 300 mg to about 900 mg.

53. A method for decreasing plasma low-density lipoprotein (LDL) cholesterol in a patient, which method comprises orally administering to the patient once per day a therapeutically effective amount of S-[2-([[1-(2-ethylbutyl)cyclohexyl]carbonyl]amino)phenyl]2-methylpropanethioate in a pharmaceutical composition with food, wherein the food is not part of the pharmaceutical composition.

54. The method of claim 53, wherein the therapeutically effective amount is about 100 mg to about 1800 mg.

55. The method of claim 54, wherein the therapeutically effective amount is about 300 mg to about 900 mg.

56. The method of claim 53, wherein the administration to the patient occurs between about 1 hour prior to consuming food to about 2 hours after consuming food.

57. The method of claim 56, wherein the administration to the patient is substantially at the same time as the consumption of the food.

58. The method of claim 56, wherein the administration to the patient is immediately after the consumption of food to up to about 1 hour after the consumption of food.

59. The method of claim 53, wherein the pharmaceutical composition is in a unit dosage form of a tablet.

60. The method of claim 59, wherein the tablet comprises about 100 mg to about 1800 mg of S-[2-([[1-(2-ethylbutyl)cyclohexyl]carbonyl]amino)phenyl]2-methylpropanethioate.

61. The method of claim 60, wherein the tablet comprises about 300 mg of S-[2-([[1-(2-ethylbutyl)cyclohexyl]carbonyl]amino)phenyl]2-methylpropanethioate, and the therapeutically effective amount is about 300 mg to about 900 mg.

62. A method for decreasing plasma LDL cholesterol and increasing HDL cholesterol in a patient, which method comprises orally administering to the patient once per day a therapeutically effective amount of S-[2-([[1-(2-ethylbutyl)cyclohexyl]carbonyl]amino)phenyl]2-methylpropanethioate in a pharmaceutical composition with food, wherein the food is not part of the pharmaceutical composition.

63. The method of claim 62, wherein the therapeutically effective amount is about 100 mg to about 1800 mg.

64. The method of claim 63, wherein the therapeutically effective amount is about 300 mg to about 900 mg.

65. The method of claim 62, wherein the administration to the patient occurs between about 1 hour prior to consuming food to about 2 hours after consuming food.

66. The method of claim 65, wherein the administration to the patient is substantially at the same time as the consumption of the food.

67. The method of claim 65, wherein the administration to the patient is immediately after the consumption of food to up to about 1 hour after the consumption of food.

68. The method of claim 62, wherein the pharmaceutical composition is in a unit dosage form of a tablet.

69. The method of claim 68, wherein the tablet comprises about 100 mg to about 1800 mg of S-[2-([[1-(2-ethylbutyl)cyclohexyl]carbonyl]amino)phenyl]2-methylpropanethioate.

70. The method of claim 69, wherein the tablet comprises about 300 mg of S-[2-([[1-(2-ethylbutyl)cyclohexyl]carbonyl]amino)phenyl]2-methylpropanethioate, and the therapeutically effective amount is about 300 mg to about 900 mg.

* * * * *

UNITED STATES PATENT AND TRADEMARK OFFICE
CERTIFICATE OF CORRECTION

| | | |
|---|---|---|
| PATENT NO. | : 7,276,536 B2 | Page 1 of 1 |
| APPLICATION NO. | : 10/802280 | |
| DATED | : October 2, 2007 | |
| INVENTOR(S) | : Urata et al. | |

It is certified that error appears in the above-identified patent and that said Letters Patent is hereby corrected as shown below:

In Claim 34, at column 17, line 56, delete "or prophylaxis"

Signed and Sealed this

Eleventh Day of March, 2008

JON W. DUDAS
*Director of the United States Patent and Trademark Office*